(12) United States Patent
Bly (10) Patent No.: US 10,754,314 B2
(45) Date of Patent: *Aug. 25, 2020

(54) SYSTEM FOR CUSTOMIZED PRODUCTION OF HAIR AND SKIN CARE PRODUCTS

(71) Applicant: Malha Bly, Houston, TX (US)

(72) Inventor: Malha Bly, Houston, TX (US)

(*) Notice: Subject to any disclaimer, the term of this patent is extended or adjusted under 35 U.S.C. 154(b) by 194 days.

This patent is subject to a terminal disclaimer.

(21) Appl. No.: 16/034,273

(22) Filed: Jul. 12, 2018

(65) Prior Publication Data

US 2019/0137957 A1   May 9, 2019

Related U.S. Application Data

(63) Continuation of application No. 15/808,861, filed on Nov. 9, 2017, now Pat. No. 10,025,280.

(Continued)

(51) Int. Cl.
| | |
|---|---|
| *G05B 15/02* | (2006.01) |
| *A61Q 5/12* | (2006.01) |
| *A61K 8/34* | (2006.01) |
| *A61K 8/42* | (2006.01) |
| *A61K 8/41* | (2006.01) |

(Continued)

(52) U.S. Cl.
CPC .............. *G05B 15/02* (2013.01); *A45D 44/00* (2013.01); *A45D 44/005* (2013.01); *A61K 8/345* (2013.01); *A61K 8/362* (2013.01); *A61K 8/416* (2013.01); *A61K 8/42* (2013.01); *A61K 8/891* (2013.01); *A61K 8/922* (2013.01); *A61K 8/9789* (2017.08); *A61Q 5/006* (2013.01); *A61Q 5/02* (2013.01);

(Continued)

(58) Field of Classification Search
CPC ...... G05B 15/02; A45D 44/005; A45D 44/00; A45D 2044/007; A61Q 5/12; A61Q 5/006; A61Q 5/02; A61K 8/345; A61K 8/42; A61K 8/416; A61K 8/922; A61K 8/891; A61K 8/362; A61K 8/9789

See application file for complete search history.

(56) References Cited

U.S. PATENT DOCUMENTS 6,516,245 B1* 2/2003 Dirksing ................ A45D 40/00
                                                              700/233
2004/0236291 A1* 11/2004 Zelickson .............. A61B 17/54
                                                              604/289

(Continued)

*Primary Examiner* — Ziaul Karim
(74) *Attorney, Agent, or Firm* — Trojan Law Offices (57) ABSTRACT

A system for cosmetologists, dermatologists, trichologists, salon professionals and the general public to produce a customized hair or skin care product using a diagnostic device for analyzing hair, scalp, and skin conditions. The diagnostic device communicates the diagnostic data to a self-contained processing apparatus, which has software that can formulate a recipe for the hair or skin care product and generate operating instructions for producing the product based on the recipe. The processing apparatus comprises a housing unit having a control center, a plurality of removable canisters capable of holding ingredients for producing the hair or skin care product, a dispensing system for dispensing the ingredients to a mixing bowl, a mixing device for mixing the ingredients, and preferably a heating element for heating the ingredients in the bowl, wherein the apparatus produces the hair or skin care product according to the operating instructions to provide individualized treatment.

11 Claims, 10 Drawing Sheets

Related U.S. Application Data

(60) Provisional application No. 62/419,594, filed on Nov. 9, 2016.

(51) Int. Cl.
| | | |
|---|---|---|
| *A61K 8/92* | (2006.01) | |
| *A61K 8/891* | (2006.01) | |
| *A61K 8/362* | (2006.01) | |
| *A61Q 5/00* | (2006.01) | |
| *A61K 8/9789* | (2017.01) | |
| *A45D 44/00* | (2006.01) | |
| *A61Q 5/02* | (2006.01) | |

(52) U.S. Cl.
CPC .......... *A61Q 5/12* (2013.01); *A45D 2044/007* (2013.01)

(56) References Cited

U.S. PATENT DOCUMENTS

| | | | | |
|---|---|---|---|---|
| 2005/0143754 | A1* | 6/2005 | Zelickson | ............... A61B 17/54 |
| | | | | 606/131 |
| 2012/0316381 | A1* | 12/2012 | Teggatz | ................... A61N 2/00 |
| | | | | 600/9 |
| 2014/0081463 | A1* | 3/2014 | Igarashi | ............. B01F 13/1063 |
| | | | | 700/265 |
| 2015/0021356 | A1* | 1/2015 | Witchell | ................ F04B 43/12 |
| | | | | 222/23 |

* cited by examiner

SYSTEM FOR CUSTOMIZED PRODUCTION OF HAIR AND SKIN CARE PRODUCTS

CROSS-REFERENCE TO RELATED APPLICATION

This is a continuation of U.S. Nonprovisional application Ser. No. 15/808,861, filed on Nov. 9, 2017, which claims the benefit of U.S. Provisional Application No. 62/419,594, filed on Nov. 9, 2016, all of which are incorporated herein by reference in their entirety for all purposes.

TECHNICAL FIELD

The present invention relates to a system for making customizable toiletry and cosmetic products, and more particularly, the invention relates to a method and apparatus for creating custom cosmetic products that are harmonized to a consumer's individual requirements based on potential of hydrogen and other factors using custom software, which can be linked to pre-existing hair, scalp and skin diagnostic devices or mobile devices. The invention also relates to an automated emulsifying machine that can communicate with a diagnostic device or mobile device to produce the customized toiletry and cosmetic products within an hour.

BACKGROUND OF THE INVENTION

Today's cosmetic and medicated hair and skin care markets are over-saturated with personal care products that are complicated and confusing. These products do not adequately cover the multitude of needs of different consumers who want to maintain or restore healthy, beautiful hair and skin. Since most consumers do not fit into just one category of hair or skin type, commercially-produced hair care and skin care products cannot treat all types of hair and skin for all individuals across the board. For example, if a consumer has fine but voluminous hair, with chemically treated ends and an oily scalp, no single commercial product can treat the combination of all such conditions. Thus, there is a need for a system and method of making customized hair and skin care products that can treat all the various unique conditions of an individual's hair and skin.

In addition to the lack of customized hair and skin treatment products, there is also a lack of customized cosmetic products. For example, Loreal has a well-known line of foundation products, but the products fail to provide an individualized approach to cosmetics other than offering foundation color. Other brands try to address customers' demand for individualized products, such as Paul Mitchell's category system, Davines' products, or even Phyto's system. However, since these brands do not adequately address the diverse needs of individual consumers, some consumers currently resort to a DIY approach by finding natural recipes on websites, such as Pinterest, YouTube, and blogs. Websites such as "Function of Beauty" and "Profile Pro" allow consumers to choose minimal customization such as color and scent online, but consumers would then have to wait days or even weeks to get the product in the mail. Even stores that offer semi-customized products do not offer high quality, organic, non-GMO (genetically modified organisms) or vegan options. Moreover, in such stores, customers often have to have an appointment to make sure a chemist is available to make the product.

Further, shampoos, conditioners, oils, lotions and other liquid toiletries are typically produced commercially in large volumes in industrial manufacturing plants. However, such commercial toiletry products often contain unwanted additives and toxic chemicals. Commercially produced shampoos, conditioners, and other toiletries on the market today contain between 10 and 30 different ingredients depending on individual hair types. The ingredients generally include surfactants, thickeners, moisturizers, conditioning agents, and additives. While not all such ingredients are harmful, some ingredients have been associated with side effects ranging from skin rashes, to breathing problems, while others have been linked to hair loss. For example, it has been reported that sodium lauryl sulphate, a surfactant or foaming agent found in nearly all shampoos, can cause allergies even in concentrations as low as 0.5%. As another example, isopropyl alcohol is a highly flammable solvent found in most cosmetics that can make the scalp very dry and cause irritation. Such chemicals have also been linked to headaches, nausea and side effects with long term exposure. Thus, it is desirable and, indeed, necessary to craft shampoos, conditioners, oils and other toiletries that do not use such toxic chemicals.

It is also desirable to produce such toiletry products based on the diagnosis of an individual's specific hair, scalp and skin conditions. For example, if the individual has seborrheic eczema, or dermatitis, which is a common inflammatory skin condition that causes flaky, scaly patches on the skin, especially the scalp (dandruff), it is advisable to use medicated shampoos that contain active ingredients that are known to combat the condition's causal agent. However, commercially-produced, off-the-shelf shampoos and conditioners not only contain toxic chemicals but are not crafted to treat the specific condition of each individual. Consequently, there is a need for a system that can produce hair or skin care products and other toiletry products that meet specific individual needs.

In an effort to craft customized shampoos, conditioners, and other toiletries for individual needs that do not use harmful chemicals, consumers have resorted to haphazardly cooking hair or skin care products at home using common kitchen tools. Although hair and skin care products can be fabricated at home on a stove top by purchasing various tools and ingredients, making such products on a stove top at home can be expensive, messy and difficult. For example, current methods for mixing granulates, powders and liquids in the kitchen are done with electric blenders. Products ranging from cakes and puddings to body butters and hair conditioners are produced using general kitchen tools. Hand mixers are currently used to combine ingredients in a pot while following a recipe. Many recipes specify that the ingredients are entered incrementally during the heating and cooling phase while stirring to emulsify. This is a time-consuming process that often does not accurately produce the desired product.

Accordingly, there is a need for an automated system to make toiletries on the spot or as needed, whether at home, in salons or at mall kiosks using natural ingredients, that is easy, efficient, fast and safe.

In addition to the need for the home production of toiletry products, there is also a demand among health care and hair care professionals for a way to produce customized products for patients and customers. Specifically, there is a need for producing shampoos, conditioners, and other toiletry products at medical clinics and hair salons (or mall kiosks) that are based on a diagnostic analysis of an individual's specific hair, scalp and skin condition. Cosmetologists, dermatologists, trichologists use a variety of diagnostic tools to analyze the hair, scalp and skin condition of patients in developing individualized treatment. Similarly, hairdressers and other salon professionals also use diagnostic tools to determine the condition of their customers' hair and scalp before a haircut or hair styling. However, even with such diagnostic analysis, cosmetologists, dermatologists, trichologists and salon professionals still have to prescribe and use commercially-made products that are not customized to the needs of their patients or customers. Thus, while such diagnostic tools are available, there is presently no system for producing customized products based on diagnostic analysis. More particularly, there is presently no system for cosmetologists, dermatologists, trichologists and salon professionals to quickly produce customized products on-site for immediate treatment following a diagnostic analysis. Accordingly, there is a need for an automated system for health care and hair care professionals to make toiletry products on-site at clinics, salons, or mall kiosks that is based on a diagnostic analysis.

There is also a need for a system to enable salon owners to produce shampoos, conditioners, and other toiletry products on-site at salons for sale to their customers. Often, for example, if salon owners want to develop and sell their own line of products, it can take weeks or even months to coordinate with a vendor or manufacturer. Thus, there is a need for a system to professionally produce specialized hair care products at salons that obviates the lead time normally required for ordering from a vendor or manufacturer.

There is also a need for a system that allows DIY hobbyists to make toiletry products at home without having to use ordinary kitchen tools. The practice of making toiletries at home has grown in recent years with the evolution of the Internet, and particularly with social media. DIY hobbyists now have access to a myriad of online DIY recipes for making customized hair care products at home with mobile devices, such as smartphones or tablets. Accordingly, there is a need for a system to make toiletry products at home that is interactive with mobile devices.

SUMMARY OF THE INVENTION

In view of the foregoing, it is an object of the present invention to provide an automated system for making toiletries that is effective for solving individual consumer concerns about hair, scalp and skin.

It is an object of the present invention to provide an automated system for cosmetologists, dermatologists, trichologists and salon professionals to craft customized toiletry products based on a diagnostic analysis of an individual's specific hair, scalp and skin conditions.

It is an object of the present invention to provide an automated system for salon owners to professionally produce shampoos, conditioners, and other toiletry products at hair salons to sell to customers.

It is an object of the present invention to provide an automated system for cosmetologists, dermatologists, trichologists to make customized hair and skin products for patients at clinics.

It is an object of the present invention to provide an automated system for hair professionals to make customized hair and skin products for customers at salons.

It is an object of the present invention to provide an automated system for individuals to make customized hair and skin products at home or at mall kiosks.

It is an object of the present invention to provide an automated system for making toiletries using diagnostic device to analyze an individual's specific hair, scalp and skin condition and converting the diagnostic analysis to a prescription for a customized toiletry product.

It is an object of the present invention to provide an automated system for making toiletries that can communicate with a diagnostic device or a mobile device.

It is an object of the present invention to provide an automated system for making toiletries by downloading a recipe from the Internet using a mobile device, which can formulate instructions to automatically produce the product.

In accordance with the objectives of the present invention, a system for producing toiletries is comprised of a processing apparatus that can communicate with a diagnostic device or a mobile device.

The diagnostic device is capable of sending data about an individual's hair or skin conditions to the processing apparatus.

The system has proprietary software capable of generating a formula to treat the identified hair or skin condition based on the data received from the diagnostic analysis. Once the processing apparatus receives the scans or data from the diagnostic device, it compares them to algorithms based on the collected data, which is delivered to a customer or a cosmetologist, dermatologist, trichologist, beauty supply owner, or someone throwing a shampoo party to make a customized hair or skin product.

Based on dermatological and trichological analyses, the software application generates a formula for producing a customized hair care product specifically suited to an individual's hair, scalp and skin conditions. For example, if the analysis indicates that there are problems with the scalp, such as dandruff or inflammatory conditions, the software application will formulate a shampoo or conditioner to treat that problem. Or if the analysis indicates damaged hair, such as caused by over exposure to heat or strong chemicals, the software application generates a formula for a shampoo or conditioner to repair the damage.

Once a formula is generated from the analysis of an individual's hair, scalp and skin condition, the software application then generates a set of operating instructions for the apparatus to produce a customized hair or skin care product.

The processing apparatus is a self-contained unit that can fit on a countertop or table top of the average household or at a clinic or salon. The processing apparatus is comprised of a plurality of canisters holding ingredients for producing hair or skin care products. The canisters, which range from 2 ounces and up, are removably stored in the housing unit. The processing apparatus has a dispensing system connected to the canisters for pumping the ingredients into a mixing bowl, where the ingredients are mixed by the mixing device according to the operating instructions. The processing apparatus has a base with a heating element for heating the ingredients (if required) in the bowl until the final product is constituted.

The current invention not only allows cosmetologists, dermatologists, trichologists to create customized hair and skin products for patients at clinics, and salon professionals to create customized hair and skin products for customers at salons, but also allows anyone to make customized hair and skin products at mall kiosks and at home.

DETAILED DESCRIPTION OF THE INVENTION

Figure 1:
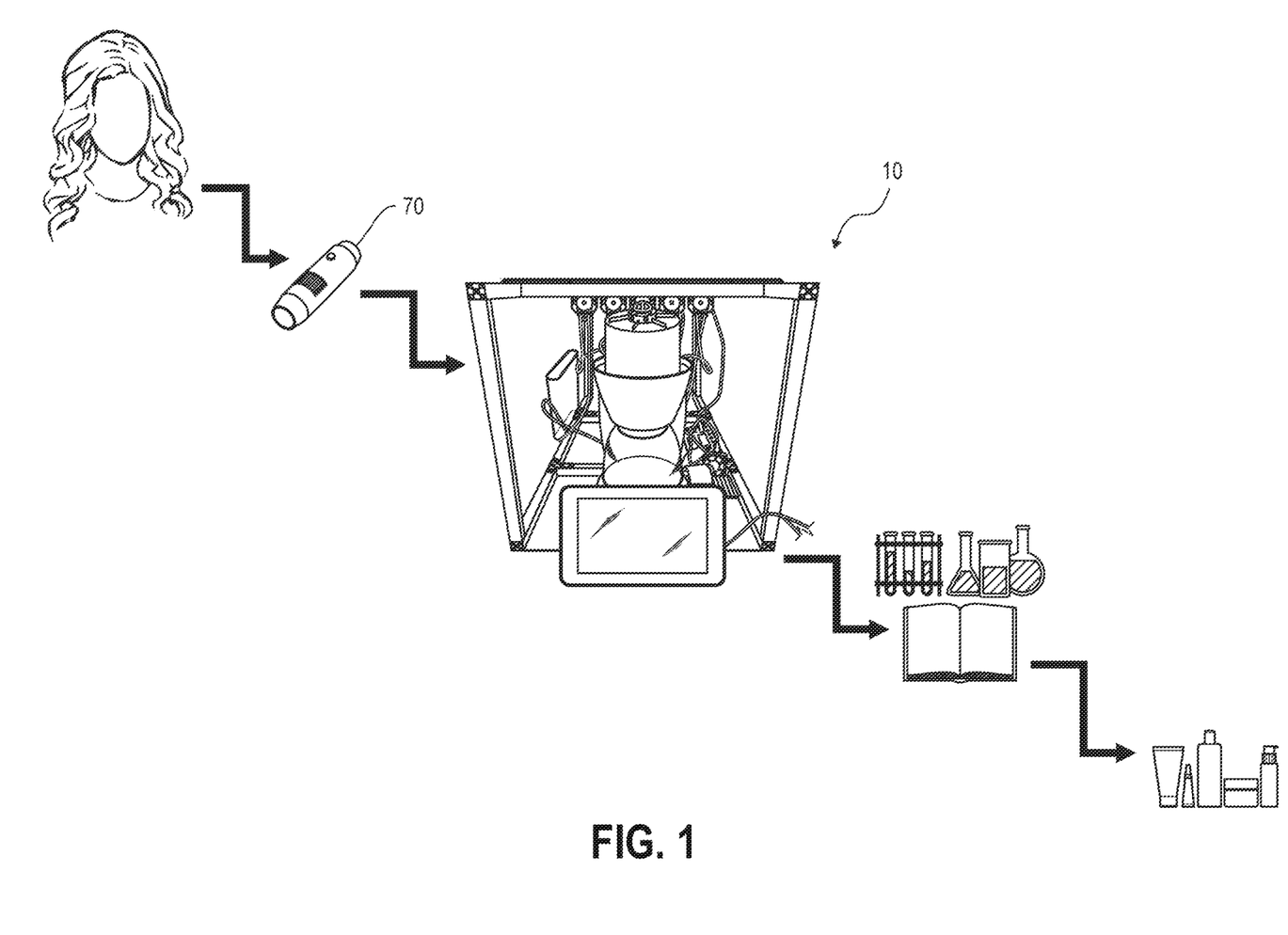
FIG. 1 is a schematic of an embodiment of the invention.

A system 1 for producing toiletries according to the present invention is shown in FIG. 1. The system 1 operates to make customized toiletries, such as hair care products, using an automated process as described herein.

Referring to FIG. 1, the system 1 is comprised of a processing apparatus 10 and a diagnostic device 70. The diagnostic device 70 is a diagnostic tool for analyzing hair, scalp and skin conditions that are known in the art. Such devices are widely used in various beauty clinic and parlors to analyze the skin and hair types of individuals. In an embodiment, the diagnostic device 70 has a camera or other micro-magnifying technology to analyze skin cells and hair follicles, including follicular properties and conditions such as pore obstruction and overactive secretion of sebum that is difficult to see with the naked eye.

Figure 3:
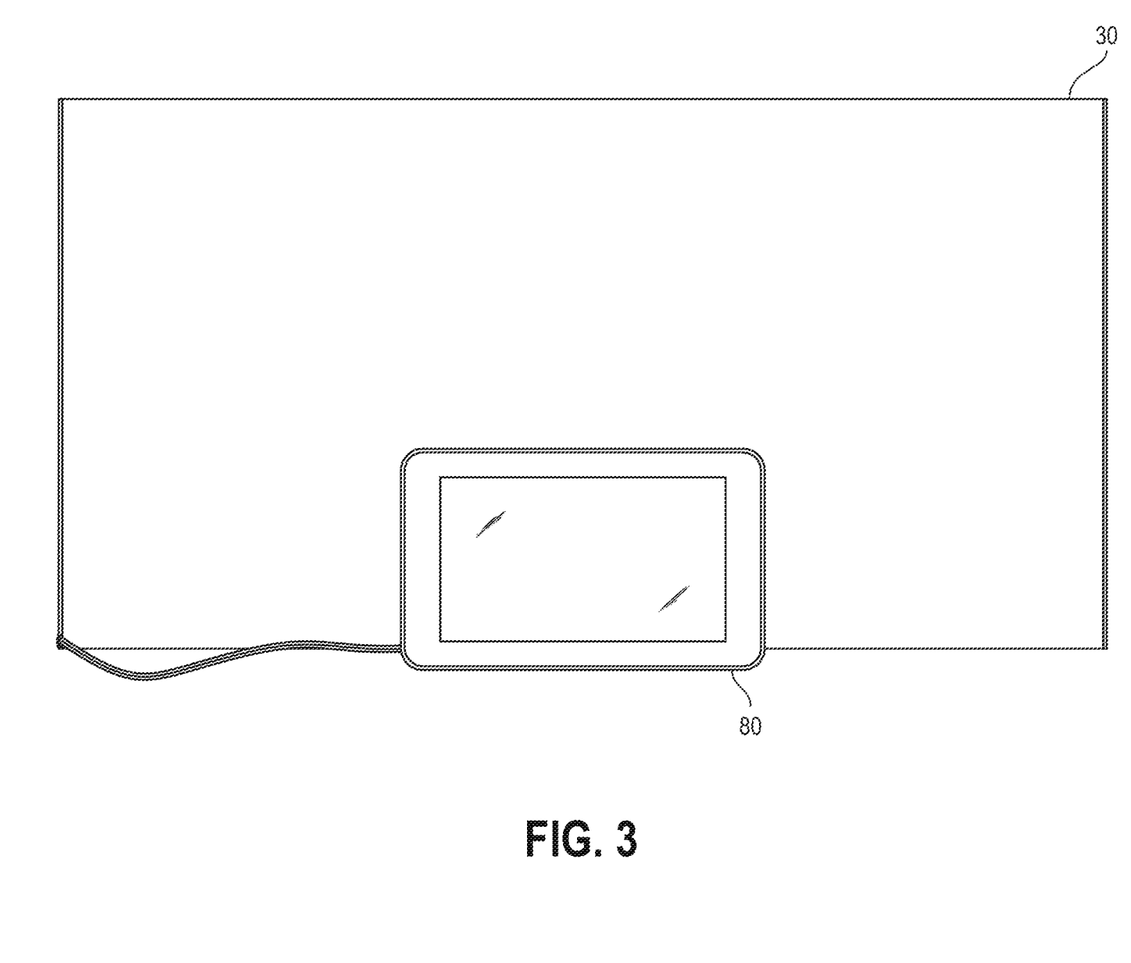
FIG. 3 is a front view of an embodiment of the invention showing a computer connected to the processing apparatus.
Figure 4:
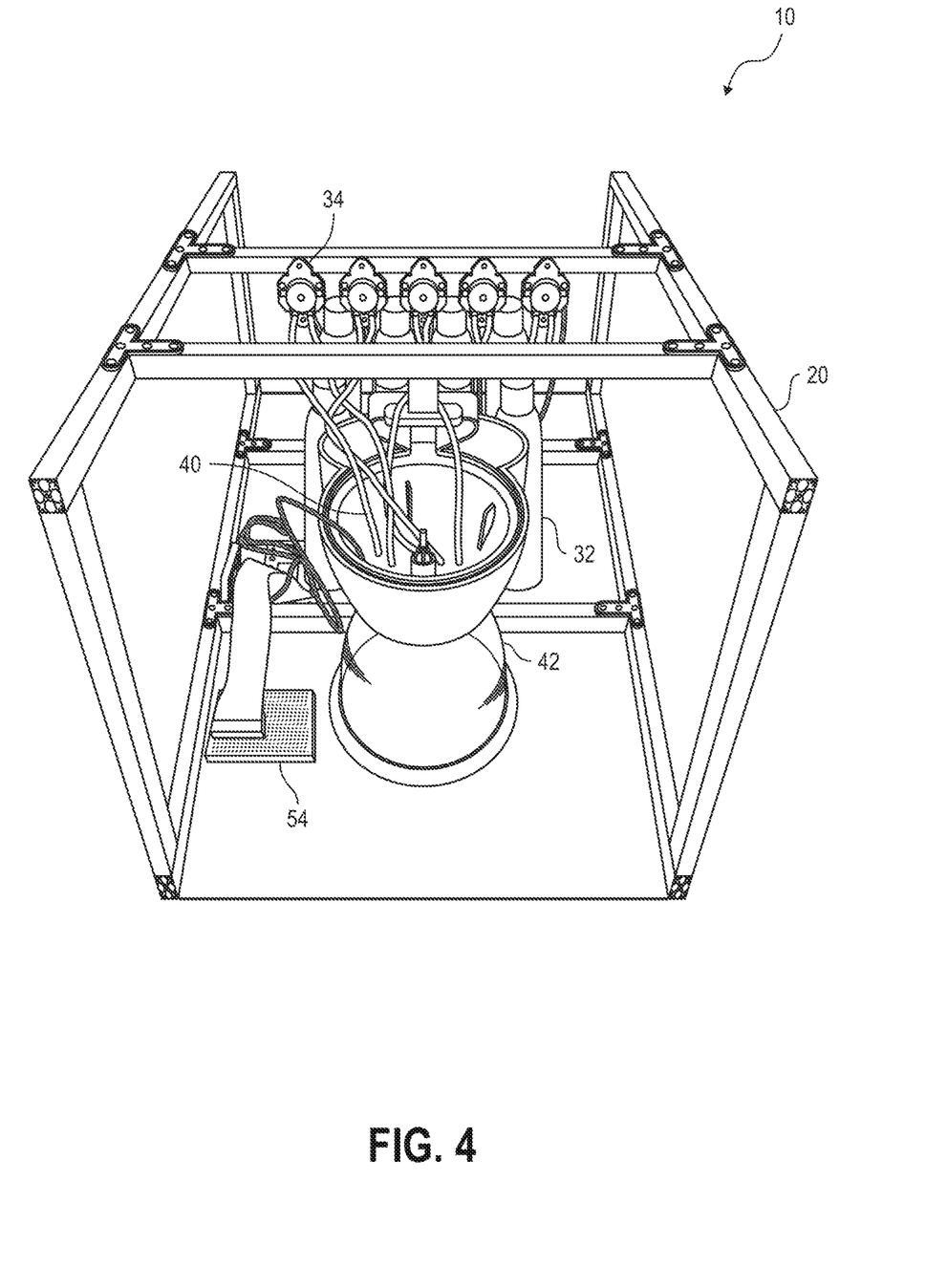
FIG. 4 is another front perspective view of an embodiment of the invention showing the internal components of the processing apparatus.
Figure 5:
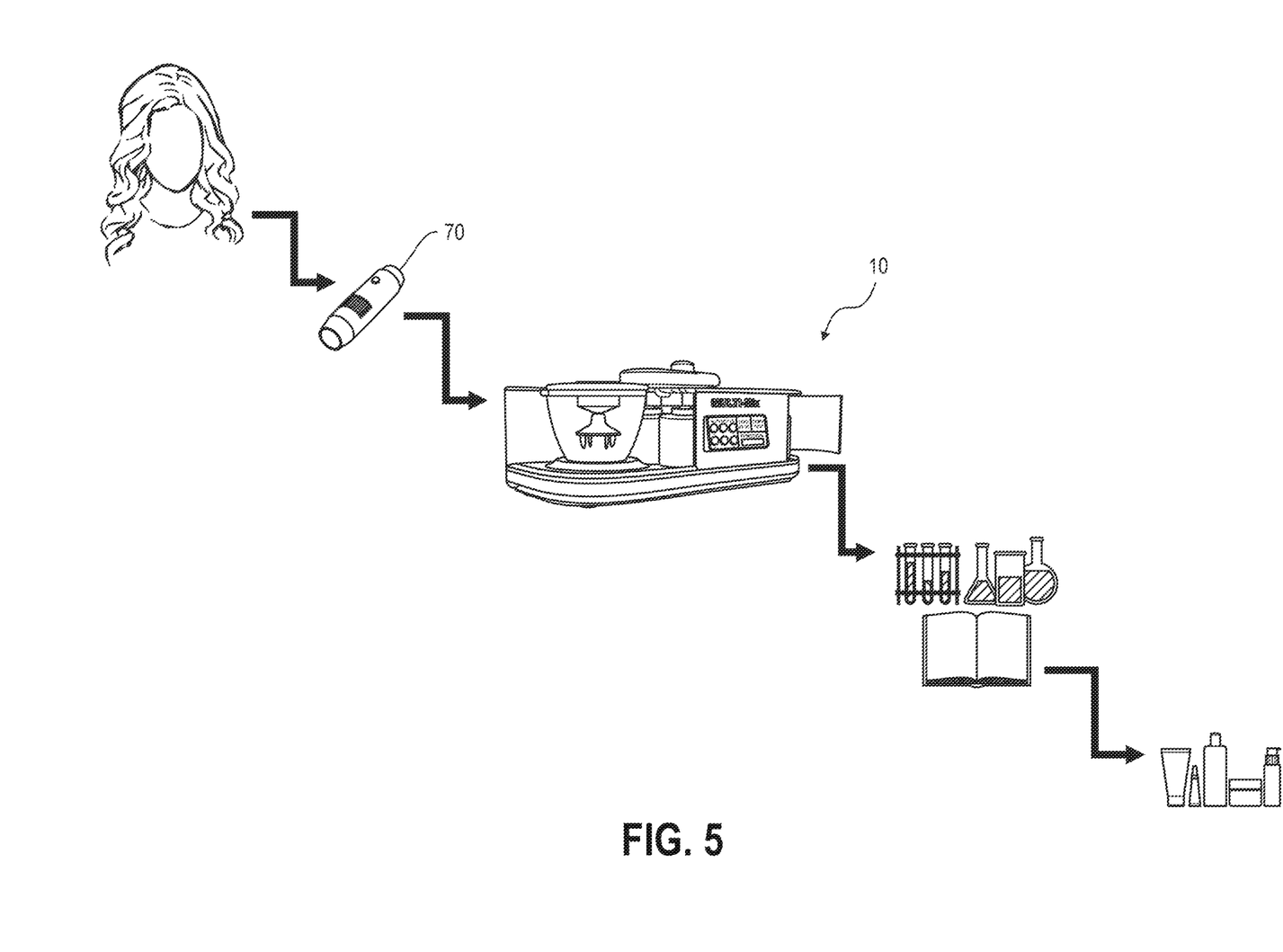
FIG. 5 is a schematic of another embodiment of the invention.

As illustrated in FIG. 4, the processing apparatus 10 is generally comprised of a housing unit 20, a plurality of canisters 32 holding ingredients for producing the product, a dispensing system 34 for delivering the ingredients, a bowl 42 for receiving the ingredients, and a mixing device 46 mixing the ingredients and other components as described herein. In the embodiment of the processing apparatus 10 shown in FIGS. 2-4, the components are housed in housing unit 20. In an alternative embodiment of the processing apparatus 10 shown in FIGS. 6-7, the canisters 32 are housed in the housing unit 20, but the bowl 42 are the mixing device 46 are not housed in the housing unit 20.

In both embodiments, the processing apparatus 10 is configured to communicate with the diagnostic device 70 preferably via wireless transmission (such as WiFi or Bluetooth protocols). Once the diagnostic device 70 conducts the diagnostic analysis, the data can be transmitted to the processing apparatus 10 by wired transmission (such as a USB port), wireless transmission (such as Bluetooth), or manual input. Based on the diagnostic data, the processing apparatus 10 has a computer 54 with proprietary software that can convert the analysis of the individual's hair, scalp and skin condition into instructions for producing a customized product.

Figure 6:
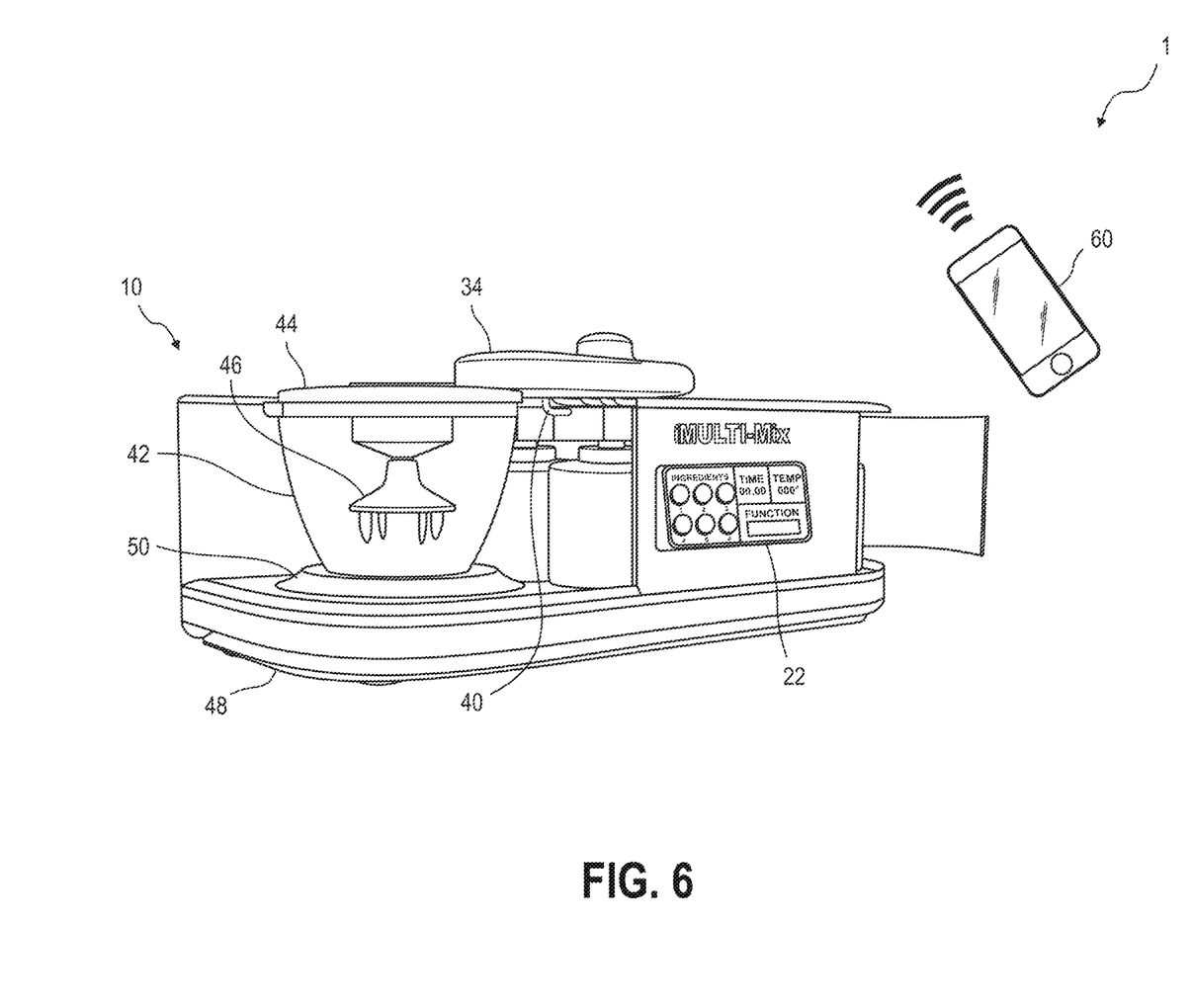
FIG. 6 is a perspective view of another embodiment of the processing apparatus.

In the alternative embodiment as shown in FIG. 6, the system 1 further comprises a mobile device 60. The mobile device 60 can download recipes from the Internet for producing the desired toiletries. The proprietary software in the processing apparatus 10 can generate a formula for customized toiletries based on the downloaded recipe. Alternatively, a user can manually input data into the processing apparatus 10 to produce customized toiletries based on the input data.

Once the processing apparatus 10 receives data from the diagnostic device 70, or from the mobile device 60, or by manual input, the software application generates a set of operating instructions for the processing apparatus 10 to produce the hair or skin product.

Figure 2:
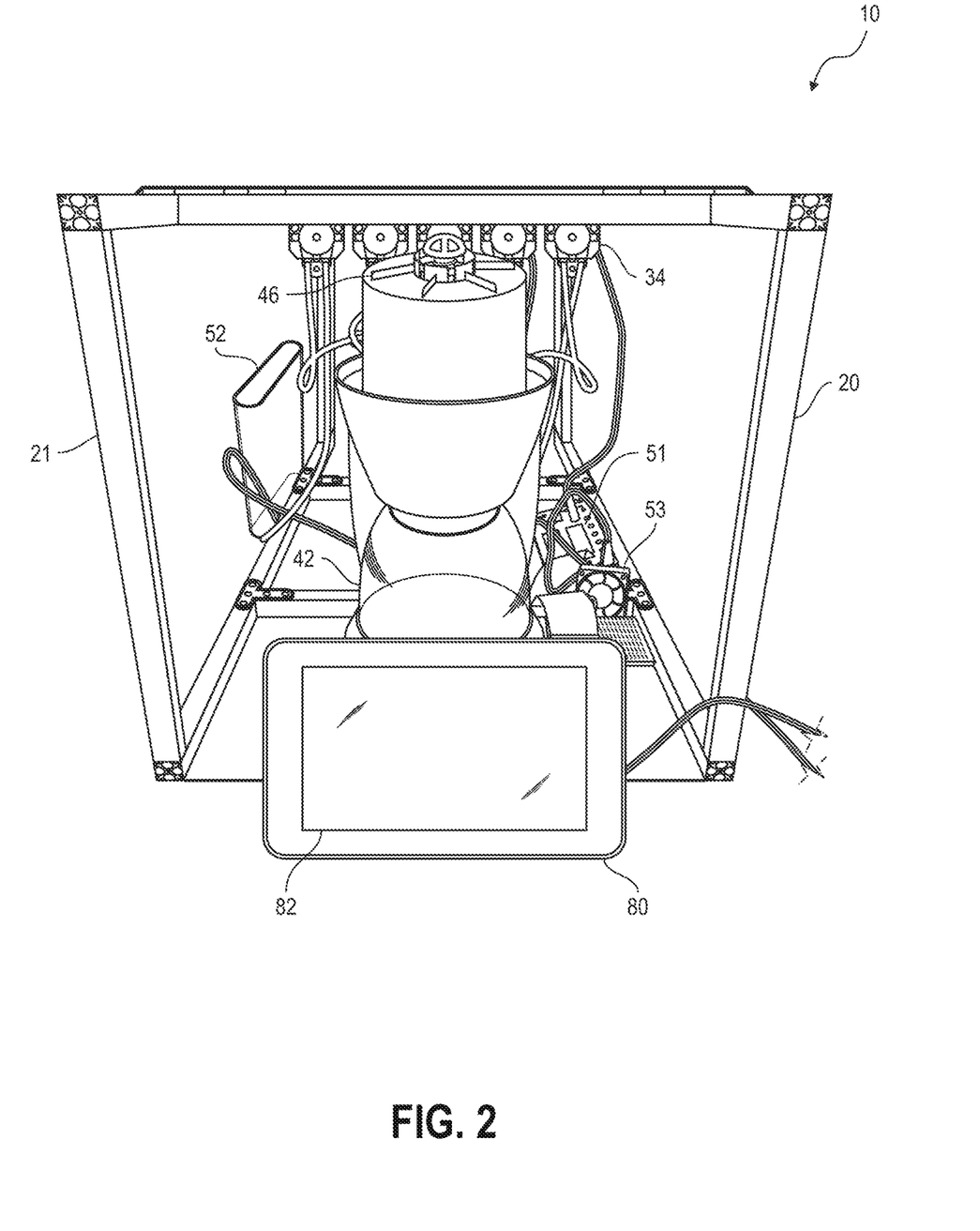
FIG. 2 is a perspective view of an processing apparatus according to an embodiment of the invention showing the internal components of the processing apparatus.

In a preferred embodiment of the invention for making a hair or skin care product as shown in FIGS. 2-4, the processing apparatus 10 is comprised of a housing unit 20 having a frame 21, a bowl 42, and a mixing device 46. The housing unit 20 has an onboard computer 54 as shown in FIG. 4 that regulates the functions of the apparatus 10. Referring to FIG. 2, the processing apparatus 10 has a computer 80 with a touch-screen 82 for displaying information (e.g., ingredient level, processing time, and temperature) and controlling the operations of the processing apparatus 10. The outside computer can be attached or mounted to a side of the housing 20 as shown in FIG. 3. In an embodiment, there can be a means for regulating the temperature of the housing unit 20 using the computer 80. For example, the apparatus 10 can have a temperature monitor 51 and cooling fan 53 for regulating the temperature of the apparatus 10.

Figure 7:
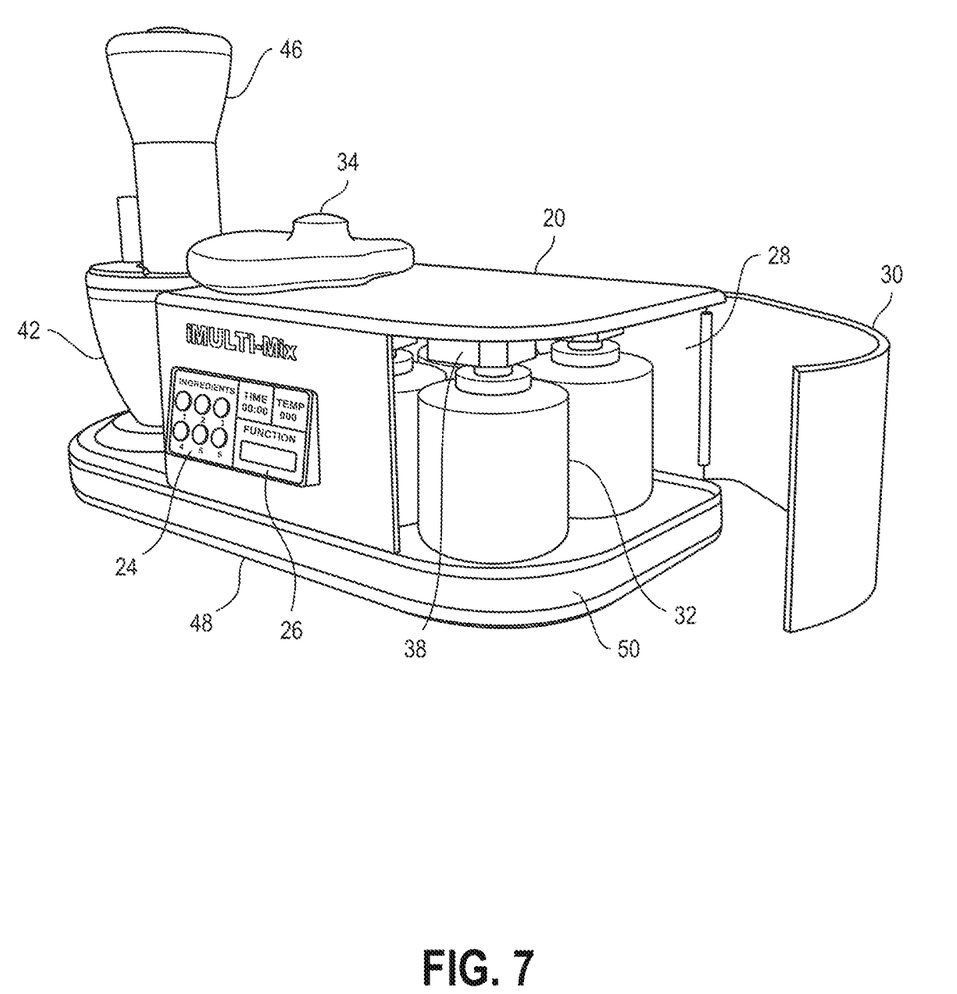
FIG. 7 is another perspective view of the embodiment of the processing apparatus in FIG. 6.
Figure 8:
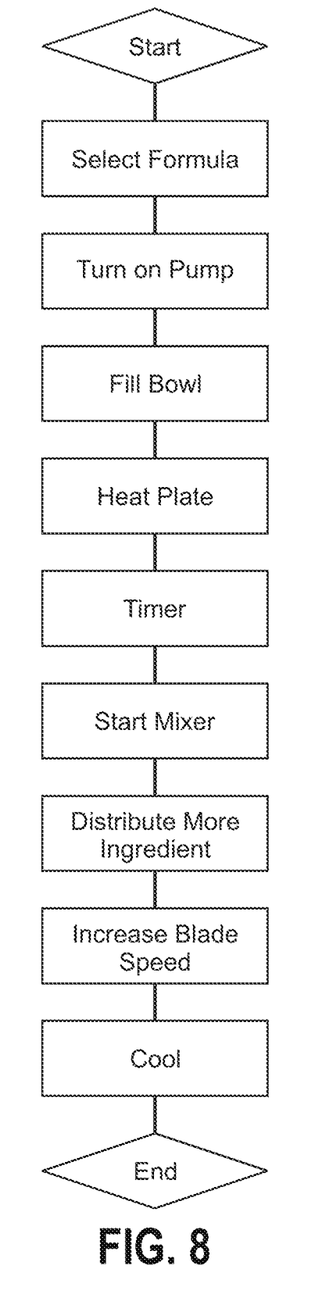
FIG. 8 is a flowchart of an operation according to an embodiment of the invention.
Figure 9:
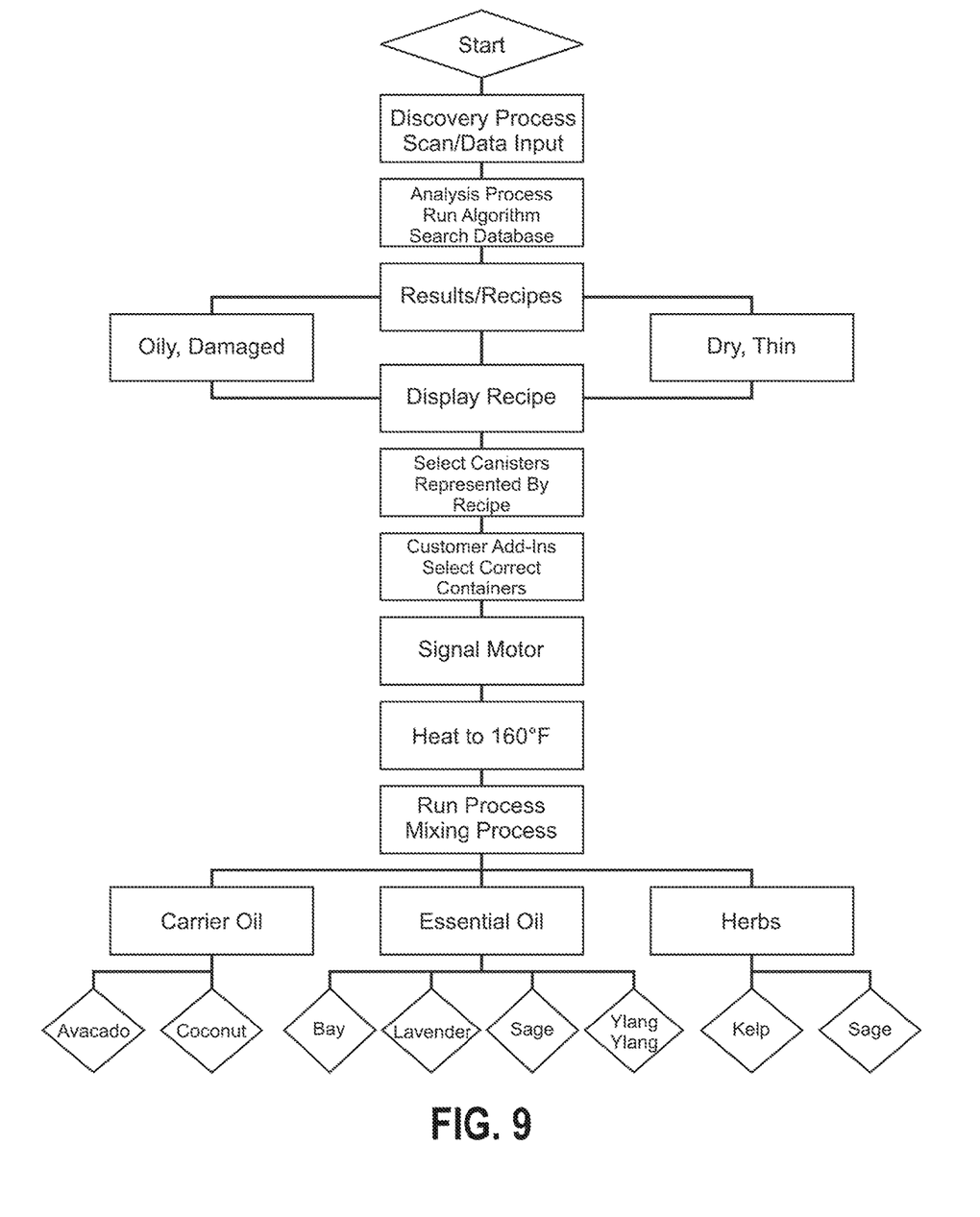
FIG. 9 is a flowchart of an operation according to an embodiment of the invention.

In an alternative embodiment of the processing apparatus 10 as shown in FIGS. 6-7, the processing apparatus 10 is comprised of a housing unit 20, a bowl 42, a mixing device 46. The housing unit 20 also has a control center 22 with controls 24 and a display screen 26 for displaying information (e.g., ingredient level, processing time, and temperature) and for controlling the operations of the processing apparatus 10. The housing unit 20 further has an internal chamber 28 preferably enclosable by a door 30. In an embodiment, there can be a means for regulating the temperature of the internal chamber 28 using the control center 22.

The processing apparatus 10 further includes a plurality of removable canisters 32 for holding ingredients to produce a hair or skin care product. Referring to FIGS. 4 and 7, the canisters 32 are removably stored in internal chamber 28 of housing unit 20. In an embodiment as shown in FIG. 7, the internal chamber 28 is capable of housing up to sixteen 2-ounce canisters 32, with each canister 32 designated to hold a particular ingredient for making the hair or skin care product. The internal chamber 28 can accommodate different numbers of canisters 32. The canisters 32 can also come in different sizes, from 2 ounces and up, to accommodate different volumes of ingredients.

The canisters are connected to a dispensing system 34 for drawing and dispensing the ingredients in the canisters 32. In an embodiment of the invention, the dispensing system 34 is comprised of conventional components known in the art, including a peristaltic pump 36 connected to tubes 40. The peristaltic pump 36 is based on alternating compression and decompression of the tubes 40 to deliver the ingredients via the tube 40 to the bowl 42. As is known in the art, the peristaltic pump 36 has a rotating shoe or roller (not shown) which passes along the length of a tube 40 to compress it. As the rotor turns, the part of the tube 40 under compression is pinched closed. In a preferred embodiment, the tubes 40 are in accordance with specifications of the peristaltic pump manufacturer so as to resist breakage or permanent deformations, and remains durable for long time and keep their original elasticity. As the tube 40 opens to its natural state after the passing of the rotor, the restitution of the tube forms a vacuum to draw the ingredients. An advantage of the peristaltic pump 36 is that it confines the ingredients to the tubing 40, so that the pump 36 does not contaminate the ingredients and the ingredients do not contaminate the pump 36. This contamination-free pumping system makes the peristaltic pump 36 particularly suitable for use in applications such as in the current invention. Further, another advantage of using the peristaltic pump 36 is that it continues to pull the ingredients from canisters 32 even if the position of the tubes 40 is higher than the position of the dispensing nozzle.

The canisters 32 are configured to be affixed to the pumps 36 by conventional methods known in the art. In the embodiment, the pump connectors 38 are located at the top of the internal chamber 28 such that the canisters 32 can be affixed to pump connectors 38 in an upright orientation. In an alternative embodiment (not shown), the pump connectors 38 can be located at the bottom of the internal chamber 28 such that the canisters 32 can be affixed to the pump connectors 38 in an upside-down orientation so that the natural force of gravity facilitates the drawing and dispensing of the ingredients from the canisters 32.

When the canisters 32 are connected to the pump connectors 38, the dispensing system 34 can be activated to pump the ingredients from the canisters 34 via the plurality of tubes 40 to the bowl 42. The pumps are controlled by the computer 80 or the control center 22 to regulate the amount of ingredients pumped from the canisters 32 and the rate of delivery of the ingredients to the bowl 42. The ingredients can be pumped from each canister 32 one at a time or from more than one canister 32 at the same time at different intervals.

The ingredients are delivered via the plurality of tubes 40 to the bowl 42 for processing. In an embodiment, the bowl 42 is enclosable with a lid 44 to prevent any accidental dispersion or spilling of the ingredients. A mixing device 46 is used to mix the ingredients in the bowl 42. The mixing device 46 can be removable or integrally connected to the bowl 42. The mixing device 46 can be controlled by control center 22 or computer 80 to regulate the speed and duration of the processing operation.

In FIG. 6, the bowl 42 sits on a base 48, which has a heating element (or heating table) 50 for heating the ingredients in the bowl 42. In an embodiment, the apparatus 10 has a sensor for detecting the temperature of the mixture in the bowl 42. The control center 22 controls when the heating element 50 is activated or deactivated, and regulates the temperature of the heating element 50.

In an embodiment depicted in FIG. 2, the apparatus 10 has a side water reservoir 52 to provide a source of water for mixing with the ingredients.

The operation of an embodiment of system 1 for producing a hair care product is now described.

In this embodiment, the diagnostic device 70 analyzes the condition of an individual's hair or skin according to the following characteristics.

Table 1 identifies characteristics of different scalp types.

TABLE 1

| Scalp Type | Characteristics |
|---|---|
| Oily | Excessive sebum production; Scalp and hair roots look oily; Depending on the texture of the hair, causes varying degrees of limpness and cohesiveness; The sebum attracts dirt and the hair appears and feels dirty quickly; Re-oiling occurs rapidly, requiring washing within 24 hours. |
| Normal/ Oily | Normal sebum production with a tendency towards oiliness; Scalp is normal and healthy; Hair appears shiny from the sufficient amount of sebum; Dirt and sebum will accumulate, requiring washing within 48 hours. |
| Normal/ Dry | Normal sebum production with a tendency towards dryness; Scalp is normal and healthy but sometimes feels dry; Hair begins to appear shiny when re-oiling begins to occur within about 48 hours after washing; Dirt begins to dull the hair 72 hours after washing. |
| Dry | Insufficient sebaceous secretion; Scalp appears taut and dry, and flaking may occur; Little or no sebum is transferred to the hair, causing it to become dull-looking and brittle; Due to lack of sebum, rarely needs to be washed, but scalp may begin to flake 96 hours after washing. |

Table 2 identifies hair conditions.

TABLE 2

| State of the Hair | Characterization |
|---|---|
| Normal | Good tensile strength, smooth cuticle and natural shiny appearance; Virgin to chemical altercation; Not significantly affected by mechanical or environmental implications. |
| Single-Processed | Chemically altered by the application of one color product, lifting no more than four levels, either all over or partially distributed by highlighting. |
| Double-Processed | Colored in with two separate procedures in which the hair is first decolorized or pre-lightened with a lightener before the depositing color is applied; Hair can become weakened and have diminished tensile strength, porosity and elasticity. |
| Naturally Curly | Genetically determined, grows in varying degrees of long twisted spirals; Shows varying diameters along each strand; Thinnest and weakest sections of the hair strand are located at the twists. |
| Permanent-Waved or Straightened | Impacted by both a mechanical action and a chemical action in which the bonds of the hair are broken and reformed in a new wavy, curly or straight state; Hair can become weakened and have diminished tensile strength, porosity and elasticity. |
| Damaged | Environmentally, mechanically and chemically altered; Loss of sheen, brittle to the touch, abraded cuticle, over-porous, and breaks easily. |

Table 3 identifies the characteristics of hair texture.

TABLE 3

| Hair Texture | Characteristics |
|---|---|
| Fine | Hair diameter is below average;<br>Lacks firmness and rigidity;<br>Subject to flyaway and tangles easily;<br>Weak and sensitive to external trauma, splitting and breaking easily.<br>Due to lack of tensile strength, tends to have difficulty holding a style. |
| Medium | Hair diameter is average;<br>Hair is both firm and soft;<br>Easy to detangle both when wet and when dry;<br>Due to good tensile strength, holds a style very well. |
| Coarse | Hair diameter is larger than average;<br>Tends to appear rougher than medium hair, but is less susceptible to external and mechanical traumas;<br>Tends to be unruly and tangles easily. |
| Very Coarse | Hair diameter is much larger than average;<br>Extremely rough to the touch and difficult to manage;<br>Resists combing, brushing and styling efforts. |

Table 5 identifies the indications of certain hair conditions.

TABLE 5

| Segment | Indication |
|---|---|
| Hair Type | Oily, Normal, Dry |
| Hair Condition | Damaged, Dry Ends |
| Texture | Fine, Normal, Coarse |
| Tensile Strength | Weak, Fragile |
| Chemical Process | Color-Treated, Permed |
| Beauty End Benefit | Volume, Curl, Straight |

Table 6 identifies the processing function based on certain characteristics.

TABLE 6

| Component | Function |
|---|---|
| Surfactant system<br>Anionic (−)<br>Amphoteric (±)<br>Nonionic (0) | Basic cleansing:<br>Blend of surfactants appropriate for specific scalp and hair cleansing needs |
| Conditioning system<br>Cationic polymers, quaternium ammonium salts (+)<br>Nonionic (e.g., silicone, ester) (0) | Basic conditioning:<br>Anti Static<br>Wet and dry compatibility |
| Ampholyte Complex (±)<br>Amphoteric surfactants<br>Amino acids<br>Proteins | Enhanced basic cleansing and conditioning:<br>Repair<br>Protect<br>Cleanse |

Once the diagnostic analysis is performed according to the above characteristics, the data from the analysis is communicated to the processing apparatus 10. The data from the analysis can also be manually inputed in the processing apparatus 10. Based on the analysis of the individual's hair, scalp and skin condition, the software application generates a formula for producing a customized hair or skin care product. For example, the software can analyze a hair sample to determine variables such texture, porosity, dryness. In this example, the ingredients for the recipe may be a combination of natural ingredients (such as olive oil, coconut oil, honey, avocado, or other natural elements) based on factors such pH balance. A suggested base formula could be as shown in Table 8 below:

TABLE 8

| Conditioner Ingredients | DRY Percentage | Use |
|---|---|---|
| Water | 80 | Solvent |
| Glicerin | 3 | Humectant/Moisture |
| DL-Panthonal | 3 | Vitamin B/preservative |
| Behenyl TM-50 | 6 | Emulsifying agent |
| Carrier Oil | 4 | Lubrication/Delivery |
| Herbs | 3 | Problem solver/preservative |
| Essential Oils | 1 | Problem solver |
| Total | 100 | |

For example, based on the data from the diagnostic analysis, the software application determines if the hair is oily or dry, thin or thick, damaged or healthy. The software application then generates a formula for producing the customized hair or skin care product based on the determination of the condition of the hair. The formula will be based factors such as pH. For example, it is known that a pH balance of 6.5 is a reference for dandruff since dandruff occurs when hair cannot hold moisture. It is also known that the pH balance also affects the tensile strength of hair. Since the formula is based on pH balance, the formula does not depend on the age or sex of the diagnostic subject for which the product is to be customized.

A formula for a shampoo could be based on the pH balance corresponding to different hair textures, for example, in Table 9:

TABLE 9

| pH Balance | Hair Texture | |
|---|---|---|
| lower | Fine | Slightly more alkaline |
| lower | Medium | Balance |
| raise | Coarse | Needs to be slightly more acidic |
| raise | Very Coarse | Needs to be slightly more acidic |

For example, a formula for a shampoo for dry hair can be based on the elements in Table 10.

TABLE 10

| Shampoo Dry | Percentage | pH balance |
|---|---|---|
| Water | 75 to 80 | The higher the pH the more the water |
| Washing agent | 5 to 10 | The higher the pH the less the detergent |
| Dimethicone | 1 | |
| Citric Acid for pH | 0.05 | |
| Essential oil | 1 | |
| Herbs | 7 to 10 | The higher the pH the more the herbs |
| Scent | .01 to .05 | |

As known in the art, the varieties of herbs that can be used to make a hair product for different conditions are identified in Table 11:

TABLE 11

| Oily absorption | Antiseptic | Astringent | Anti-Dandruff | Moisturizer | Softener |
|---|---|---|---|---|---|
| Peppermint | Thyme | Peppermint | Jojoba oil | Jojoba oil | Jojoba oil |
| Bergamot | Chamomile | Chamomile | Olive oil | Chamomile | Avocado |
| Witch hazel | Comfrey | Rosemary | Rosemary | *Aloe vera* | Rosemary |
| Basil | Lemongrass | Witch hazel | Hysop | Basil | Grapeseed oil |
| Yarrow | Tea tree oil | Tea tree oil | Tea tree oil | Apricot oil | *Papaya* |
| *Eucalyptus* | *Eucalyptus* | Lavender | *Eucalyptus* | Lanolin | Lavender |
| Lemongrass | Myrrh | Yarrow | Burdok root | Almond oil | *Ginseng* |
| Rosemary | Sage | Sage | Sage | Comfrey | Sandalwood |
| Thyme | Lemon juice | Lemon juice | Golden seal | Castor oil | Glycerin |

| Conditioner | Hair Loss | Hair Growth | Cell Rejuvenator | Scalp Soother |
|---|---|---|---|---|
| Kelp | Jojoba oil | Kelp | Emu oil | *Aloe vera* |
| Nettle | Nettle | Nettle | Rose hip seed oil | Carrot oil |
| Rosemary | Rosemary | Rosemary | Comfrey | Comfrey |
| Almond oil | Black seed oil | Black seed oil | Lavender | Sage |
| Burdok root | Olive oil | Dandelion | *Echinacea* | *Eucalyptus* |
| Lavender | Kelp | *Aloe vera* | | Avocado |
| *Eucalyptus* | Horsetail | Basil | | Jasmine |
| Sage | Sage | Horsetail | | Almond oil |
| Thyme | Thyme | Thyme | | Chamomile |

After a formula for the hair or skin is selected, instructions are generated for producing the product.

In accordance with the instructions, the dispensing system 34 is activated. The dispensing system 34 functions to pump a select amount of ingredients from the canisters 34 based on the diagnostic data of the hair, scalp, and skin conditions. The ingredients are pumped via the tubes 40 to the bowl 42. The dispensing system 34 can dispense precise amounts of ingredients at relevant time intervals as prescribed by the instructions from the software.

When the ingredients are delivered to the bowl 42, the heating plate 50 heats the ingredients in the bowl 42 to a temperature prescribed by the operating instructions. The ingredients are then mixed in the bowl 42 by the mixing device 46 according to a speed, mode, and duration prescribed by the operating instructions. The cycle of operation can be repeated as necessary according to the operating instructions. For instance, additional ingredients can be dispensed and mixed at a different speed for a different duration. Once the operation cycles are completed, the mixture is cooled. The cooled mixture constitutes a hair care product that is customized according to the recipe. The processing apparatus 10 then signals when the product is complete.

An example of the processing for a product is shown in Table 12.

TABLE 12

| Process Step ID | Process Step Description | Next Step ID | Shape Type |
|---|---|---|---|
| P100 | Start | P101 | Start |
| P101 | Discovery Phase | P102 | Process |
| P102 | Analysis Phase | P103 | Subprocess |
| P103 | Results/Recipe | P104 | Document |
| P104 | Display Recipe | P105 | Document |
| P105 | Choose Add-ins | P106 | Process |
| P106 | Add container 1 | P107 | Process |
| P107 | Add container 2 | P108 | Process |
| P108 | Add container 3 | P109 | Process |
| P109 | Add container 4 | P110 | Process |
| P110 | Start Mixing | P111 | Process |
| P111 | Temp Control | P112 | Process |
| P112 | HOLD Temp | P113 | Process |

TABLE 12-continued

| Process Step ID | Process Step Description | Next Step ID | Shape Type |
|---|---|---|---|
| P113 | Timer Control | P114 | Process |
| P114 | Release Temp | P115 | Process |
| P115 | Temp Sensor | P116 | Process |
| P116 | Add container 7 | P117 | Process |
| P117 | Add container 9 | P118 | Process |
| P118 | Add container 10 | P119 | Process |
| P119 | Add container 13 | P120 | Process |
| P120 | Stop Mixing | P121 | Process |
| P121 | Temp Sensor | P122 | Process |
| P122 | Signal complete | 0 | END |

Figure 10:
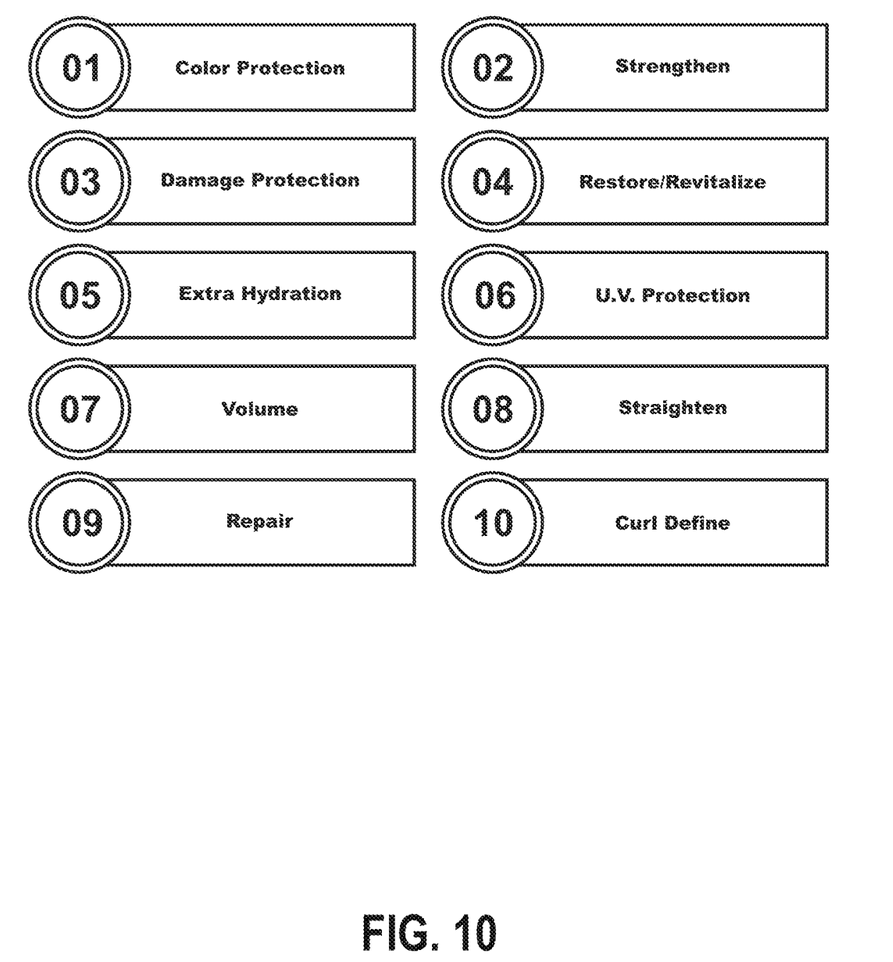
FIG. 10 illustrates the formula options of an embodiment of the processing apparatus.

In an embodiment, as shown in FIG. 10, the processing apparatus can display the options for creating a formula. The options displayed on the processing apparatus include, but not limited to, color protection, strengthen, damage protection, restore/revitalize, extra hydration, U.V. protection, volume, straighten, repair, and curl define.

In another embodiment of the invention, the software application can download a recipe for a hair care or skin product from the Internet, and generate operating instructions for the production of the hair care or skin product based on the recipe. Alternatively, a user could also manually input operating instructions based on the recipe. In this embodiment, the system 1 can produce the hair or skin care product with or without analyzing an individual's scalp and hair condition.

The system for providing customized hair, skin and scalp solutions for individual consumers according to the present invention provides cosmetologists, dermatologists, trichologists, salon professionals and consumers with the ability to create customized products that customers want and, at the same time, reduces carrying costs, eliminates waiting for orders to arrive, and prevents use of the wrong product. In most cases, the customized product can be produced in less than one hour while a customer is getting other services at a salon or clinic. The system for producing customized hair and skin products also offers security to those who are allergic to gluten or other chemicals found in commercially produced hair or skin products made by large manufacturers. The system gives the customer tremendous flexibility and can be produced in sized as little as 8 oz and as large as 32 oz according to customers' demand, thereby eliminating waste.

The above-described embodiment is merely illustrative of the principles of the present invention. It will be apparent to those skilled in the art that other embodiments may be devised without departing from the scope of the invention, as defined in the following claims.

I claim:

1. A system for producing a customized hair or skin care product, said system comprising:
    a diagnostic device for analyzing scalp or hair condition, said diagnostic device having a transmitter for communicating data of said scalp or hair condition;
    an apparatus for creating said hair or skin care product to treat said scalp or hair condition based on said data received from said diagnostic device, said apparatus comprising:
        (i) a receiver for receiving said data from said diagnostic device;
        (ii) a control unit programmed to generate a formula to treat said scalp or hair condition based on said data received from said diagnostic device;
        (iii) a housing unit;
        (iv) a plurality of removable canisters housed in said housing unit, said removable canisters capable of holding ingredients for producing said hair or skin care product;
        (v) a dispensing system connected to said canisters for dispensing said ingredients according to said formula;
        (vi) a bowl for receiving said ingredients dispensed from said dispensing system according to said formula;
        (vii) a mixing device for mixing said ingredients in said bowl according to said formula;
        (viii) a base having a heating element for heating said ingredients in said bowl according to said formula;
    wherein said diagnostic device communicates said data of said scalp or hair condition to said control unit of said apparatus;
    wherein said control unit operates said dispensing system, said mixing device, and said heating element to produce said customized hair or skin care product to treat said identified hair or skin condition.

2. The system for producing a customized hair or skin care product of claim 1, having a software application capable of formulating instructions for the production of a hair or skin care product based on a recipe.

3. The system for producing a customized hair or skin care product according to claim 1, wherein said canisters can be removed from said housing unit to be filled and refilled with said ingredients.

4. The system for producing a customized hair or skin care product according to claim 1, wherein data from said diagnostic analysis can be manually input into said apparatus.

5. The system for producing a customized hair or skin care product according to claim 1, wherein data from said diagnostic analysis can be electronically communicated to said apparatus.

6. The system for producing a customized hair or skin care product according to claim 1, wherein said dispensing system comprises:
    a peristaltic pump connected to said canisters for pumping said ingredients from said canisters to said bowl;
    a plurality of tubes for delivering said ingredients to said bowl.

7. The system for producing a customized hair or skin care product according to claim 1, wherein said mixing element is removably attachable to said enclosable bowl.

8. The system for producing a customized hair or skin care product according to claim 1, wherein said mixing element is capable of operating at variable speeds.

9. The system for producing a customized hair or skin care product according to claim 1, wherein said bowl is enclosable by a lid.

10. The system for producing a customized hair or skin care product according to claim 1, wherein said control unit regulates said dispensing, mixing, and heating of said ingredients.

11. A method for using the system for producing a customized hair or skin care product of claim 1, wherein said method comprises the steps of:
    (i) analyzing hair or scalp conditions using said diagnostic device;
    (ii) identifying said data for specific hair or scalp conditions;
    (iii) communicating said data to said apparatus for producing said customized hair or skin care product;
    (iv) generating said formula to treat said identified hair or skin condition using a software;
    (v) generating operating instructions to produce said customized hair or skin care product based on said formula;
    (vi) dispensing said ingredients according to said operating instructions;
    (vii) mixing said ingredients according to said operating instructions;
    (viii) heating said ingredients according to said operating instructions;
    wherein, said steps are repeated as necessary according to said operating instructions;
    whereby, said hair or skin care product is customized according to said operating instructions.

* * * * *